United States Patent [19]

Knoll et al.

[11] Patent Number: 4,546,255

[45] Date of Patent: Oct. 8, 1985

[54] ENERGY WINDOW SELECTION FOR A RADIATION SIGNAL PROCESSING SYSTEM

[75] Inventors: Glenn F. Knoll; Mark E. Schrader, both of Ann Arbor, Mich.

[73] Assignee: Medtronic, Inc., Minneapolis, Minn.

[21] Appl. No.: 367,245

[22] Filed: Apr. 12, 1982

[51] Int. Cl.⁴ ............................ G06F 7/38; G01T 1/20
[52] U.S. Cl. ...................................... 250/369; 364/414
[58] Field of Search ................. 250/252.1, 363 S, 369; 364/414, 415

[56] References Cited

U.S. PATENT DOCUMENTS

| | | | |
|---|---|---|---|
| 3,011,057 | 11/1961 | Anger | 250/363 S |
| 3,745,345 | 7/1973 | Muehllehner | 250/363 S |
| 4,060,730 | 11/1977 | Zioni et al. | 250/369 |
| 4,095,108 | 6/1978 | Inbar et al. | 250/369 |
| 4,179,607 | 12/1979 | Lange et al. | 250/363 S |
| 4,212,061 | 7/1980 | Knoll et al. | 364/414 |
| 4,281,382 | 7/1981 | Knoll et al. | 250/363 S X |
| 4,386,404 | 5/1983 | Knoll et al. | 250/363 S X |

OTHER PUBLICATIONS

Lapidus, A New Method of Correcting for Detector Non-Uniformity in Gamma Cameras, Nov. 77.
Spector et al., Analysis and Correction of Spatial Distortions Produced by the Gamma Camera, vol. 13, No. 5, Journal of Nuclear Medicine, 1971.

*Primary Examiner*—Alfred E. Smith
*Assistant Examiner*—Richard Hanig
*Attorney, Agent, or Firm*—Merchant, Gould, Smith, Edell, Welter & Schmidt

[57] ABSTRACT

An improved method and apparatus for energy window selection in a radiation signal processing system which in a preferred embodiment includes obtaining energy level histograms corresponding to corrected spatial elements and determining a standard count of radiation events to be accepted by each true spatial element in response to a flood image. The energy window of each corrected spatial element is then adapted to cause each to accept the standard count of radiation events in response to a flood image whereby greater uniformity of image may be accomplished in the imaging process.

17 Claims, 6 Drawing Figures

ENERGY WINDOW SELECTION FOR A RADIATION SIGNAL PROCESSING SYSTEM

TECHNICAL FIELD OF THE INVENTION

This invention relates to the field of nuclear imaging systems in medicine and more particularly to the processing of signals from gamma ray cameras.

BACKGROUND OF THE INVENTION

Nuclear medicine is one of the most rapidly developing fields of clinical investigation. The term deriving from its origin in nuclear physics involves administration by injection into a vein of a small dose of radioisotope (a radioactive substance emitting gamma rays). The bloodstream distributes the dose throughout the body and a suitably sensitive transducer records a history of this distribution.

Areas of the body having high "uptake" of the isotope or a rich blood supply show up as bright or highly illuminating sources while conversely those of low "uptake" or blood supply appear dark. In this manner any portion of the body or specific organ may be subjected to clinical investigation in a safe, reliable and noninvasive manner.

The most frequently employed nuclear investigation device is a radiation transducer having a scintillation crystal (i.e. one that emits light photons proportionately to received radiation energy quanta). The light photons are detected by a plurality of phototubes in close optical communication with the crystal generating electric signals indicative of the light's source and intensity. Cameras of this variety are generally referred to as an "Anger" or gamma ray cameras. U.S. Pat. No. 3,011,057, incorporated herein by reference, discloses such a device.

When exposed to a radioactive source, a scintillation camera of this type produces an image of the isotope distribution by recording the phototube outputs corresponding to the incidence of individual gamma rays on the crystal. The phototube outputs are interpreted and translated by electronic circuitry into orthogonal (X, Y) spatial coordinates and a third signal (Z) representative of the energy level of each gamma ray event. The energy Z signal is particularly useful for screening or filtering out unwanted detections which result from background radiation, scattering, etc. By establishing an energy window around the energy level known to be typical of the nuclide sought to be detected the desired X, Y and Z signals may be accepted for processing while unwanted signals are rejected.

A well known problem of gamma cameras relates to the inherent nonlinearities of camera design and construction. The nonlinearities, which are exacerbated with attempts to increase camera resolution, result in spatial distortion of image points. This distortion results in both nonlinearity and nonuniformity of image. In general, nonlinearity may be attributed to (X,Y) signal distortion. Nonuniformities can arise either from these same distortions or from variance in Z signal response as a function of (X, Y) source position. These spatially related inherent sources of image distortion may be corrected in various ways. U.S. Pat. No. 3,745,345, discloses one attempt to correct spacial non-linearities. However it has been found that the method disclosed therein creates further artifacts that distort the images. In U.S. Pat. Nos. 4,212,061 and 4,281,382 (which have a common assignee to the present application) X and Y correction factors are derived and stored for employment in correcting camera signals on-line while the image is being acquired.

As made clear by U.S. Pat. Nos. 4,212,061 and 4,281,382, incorporated herein by reference, the differences in Z signal, as a function of the source position, are of significance in correcting distortion due to nonuniformity of image. Accordingly, the above-identified patents disclose a procedure or method of normalizing the camera Z response as a function of source position. The method, which is described in detail in the patents, involves acquiring a separate energy histogram for each unique (X, Y) element of the camera image. The elements are defined by a 64×64 matrix in apparent space i.e. the uncorrected (X,Y) camera response. The histogram includes the number of counts and their associated energy level for each element. A standard search and fitting routine may be applied to the accumulated data to determine the peak, about which a low Z threshold value and a high Z threshold value are determined to define a window. These values are placed in a Z translation table having unique threshold pairs for each of the apparent space 64×64 matrix elements. The nonuniform response of the camera to gamma ray energy levels may then be compensated for according to which element the event originates in. By controlling how the Z threshold window is defined, one is able to not only maximize the detection of significant information but minimize recording of unwanted events.

The above-described method provides effective means for accepting, according to the apparent element of origination, only those (X,Y) signals having energies which will contribute to the construction of a meaningful picture or image; the present invention extends and improves that method by modifying how the energy selection or window is determined.

SUMMARY OF THE INVENTION

The present invention provides an improved apparatus and method for selecting only meaningful information from signals produced by suitable transducers and in particular Anger-type radioisotope cameras producing positional information. Specifically, the present invention is an improvement in the means for determining energy threshold values as a function of radiation event positional information disclosed in U.S. Pat. Nos. 4,212,061 and 4,281,382.

In the present invention, in one embodiment, the establishment of the energy threshold table begins by flooding the camera face with an uniform source of radiation and utilizing the pre-established spatial translation table to reposition detected radiation events according to their true spatial element coordinates. A histogram is compiled for each true spatial element, the histogram comprising the number of radiation events occurring at a plurality of discrete energy levels. A peak centroid value is then determined for each element, and an initial energy window is set. Next, a specified region of the camera field of view, usually the center of the image is inspected to determine a target sum of radiation events to be accepted by each element whereby a standard is set for adjusting the energy windows of each element. Using the standard, the energy window for each element is progressively adapted so that every element will accept nearly the same number of radiation events or counts in response to a flood or calibration image. Finally, the energy window for each true spatial element is translated back to its apparent spatial element and incorporated into a energy threshold table accessible by the apparent spatial coordinates of each radiation event. The energy windows thus established and incorporated into a radiation signal processing system of the type disclosed in U.S. Pat. Nos. 4,212,061 and 4,281,382 provide for greater uniformity of image than previously achievable.

It should be clear that the invention is not dependent on the particular numbers used to define the true space, that is, any corrected coordinate system that differs from the true space coordinate system by a predetermined value or values is equivalent to the true space coordinate system, since the difference can be accounted for at any point in the correction process simply by adding or subtracting the known predetermined value or values to the coordinate system. Thus although for ease of understanding, the (U,V) space is referred to as "true" space or similar terminolgy, it is understood that corrected space using corrected coordinates can also be used in the invention. In this specification "corrected" and "true" will be used interchangeably. The term "true" is used for ease of understanding however the broader concept "correct" is intended.

The foregoing digital technique and method provides improved imaging capability by eliminating to a great degree nonuniformities due to spatial variation in the camara energy level detection response.

Other objects and aspects of the invention will become clear upon consideration of the detailed description of the invention in conjunction with the drawings.

DETAILED DESCRIPTION OF THE PREFERRED EMBODIMENT

To facilitate the understanding of the present invention a brief review of the methods and apparatus disclosed in U.S. Pat. Nos. 4,281,382 and 4,212,061, hereinafter referred to as the prior system, will be given.

Figure 1:
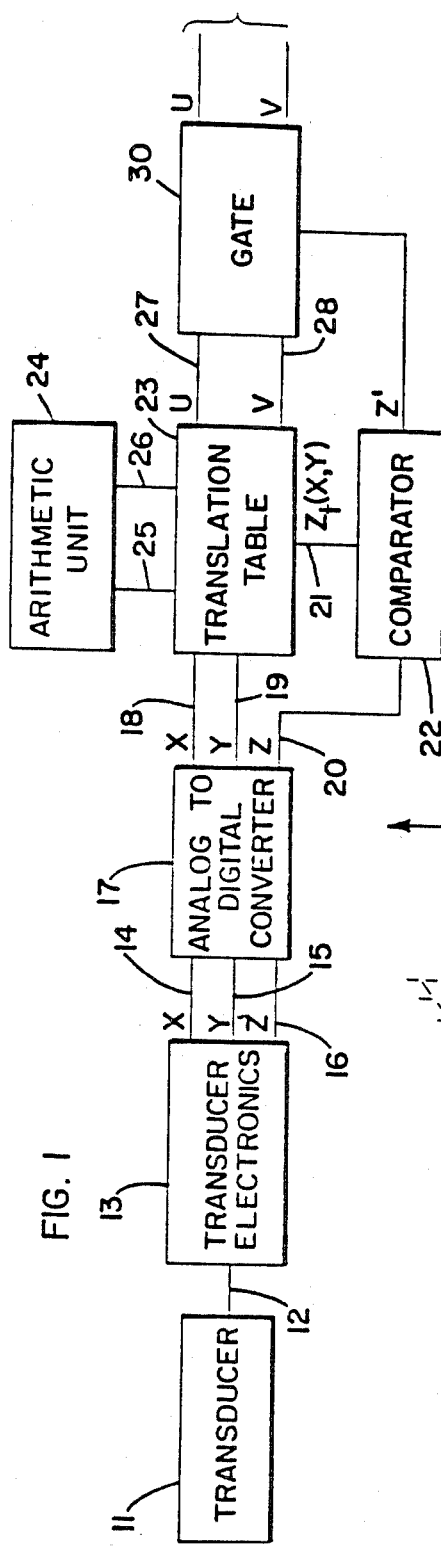
FIG. 1 is a functional block diagram for the system of the present invention.

Referring to FIG. 1, which assumes interconnection with the computer, the radiation imaging apparatus of the prior system is depicted in functional block diagrammatical form. Transducer 11 is a gamma camera similar to that described in U.S. Pat. No. 3,011,057 and detects radiation events eminating from external source. Camera output signal 12 is operated on by camera electronics 13 to provide orthogonal spatial coordinates X 14 and Y 15 and energy signal Z 16. These analog signals are then digitized in an analog to digital converter 17 producing preferably twelve (12) bit X and Y words 18, 19 respectively, and preferably an eight (8) bit Z signal. The 12 bit X and Y words are comprised of 6 MSB's (most significant bits) defining the element of origin in a 64×64 matrix and 6 LSB's (least significant bits) defining the precise location within the element for each detected event.

Coordinate signals (X, Y) are corrected to their corrected or true coordinate U (27) and V (28) values respectively (or any equivalent space, such as any space differing from the true space by a predetermined value or values) by accessing translation table 23, with the 6 MSB's of the (X, Y) signals. Table 23 comprises linear rectangular matrix arrays containing U,V values addressed by their respective corresponding X, Y coordinates and performing interpolation routines in arithmetic unit 24 with respect to the 6 LSB's of the (X, Y) signals. Processor signals 25, 26 represent information going into and out of arithmetic unit 24 during the performance of specifically called up routines. Translation table 23 also furnishes a pair of selected energy threshold signals $Z_t$ 21 for the particular apparent (X, Y) coordinates of detected radiation events. The energy level of Z signal 20 is compared with the $Z_t$ signals 21 in comparator 22 and if found within the appropriate range, i.e. between acceptable window limits gate signal Z' (Z prime) is generated and gate 30 allows each acceptable energy event to be recorded and displayed at corrected coordinates (U, V.)

Figure 6:
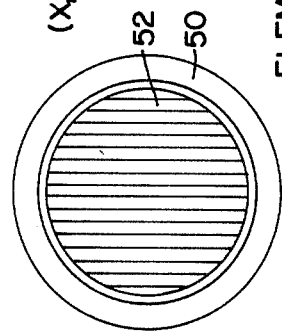
FIG. 6 is a plan view of a calibration plate.

The calibration procedure used in both the prior system and the present invention which is required to furnish the spatial coordinate correction data may be summarized as follows. A precision grid, for example the one shown in FIG. 6, is positioned over the camera face and the camera then subjected to a source of radiation positioned essentially at infinity. Grid 50 has approximately 18 to 20 lines or gaps 52 formed therein, each line having dimensions selected so that its apparent width is determined primarily by the spatial resolution of the camera, viz, a width of approximately 3 mm and center to center spacing of approximately 15 mm. As described in the patents corresponding to the prior system this provides a known image to the camera scintillation crystal, whereby any deviation or distortion in camera spatial (X, Y) response may be determined. With grid 50 positioned over the camera face so that image lines (52) 1 thru n are in a substantially vertical orientation, a pair of ADC (analog to digital converter) values ($X_n$, $Y_i$) corresponding to one of 64 equally spaced orthogonal profiles or Y positions is selected for determination of a corresponding entry in the spatial correction tables. Events are detected at each of the $X_n$ image lines corresponding to profile $Y_i$, and data representing a one dimensional profile through the image with event peaks at each line is generated. The centroid $X_c$ of each peak is then determined. This provides $X_c$ values for the uniformly spaced known U values of the calibration image. This data is then spline fit to derive a relation of $U = ax^3 + bx^2 + cx + d$. Based on this relationship, U values for preferably 64 predetermined X coordinates are determined. In the same manner relationships are derived for preferably 64 values of $Y_i$. The entire procedure is then repeated, after rotating grid 50 by 90°, to derive a best fit expression of $V = ey^3 + fy^2 + gy + h$ for all 64 values of $X_i$ and then the entire spatial corrective data is entered into the translation tables i.e. U and V values as functions of 64 X, Y coordinate locations in the rectangular matrix arrays.

Figure 3:
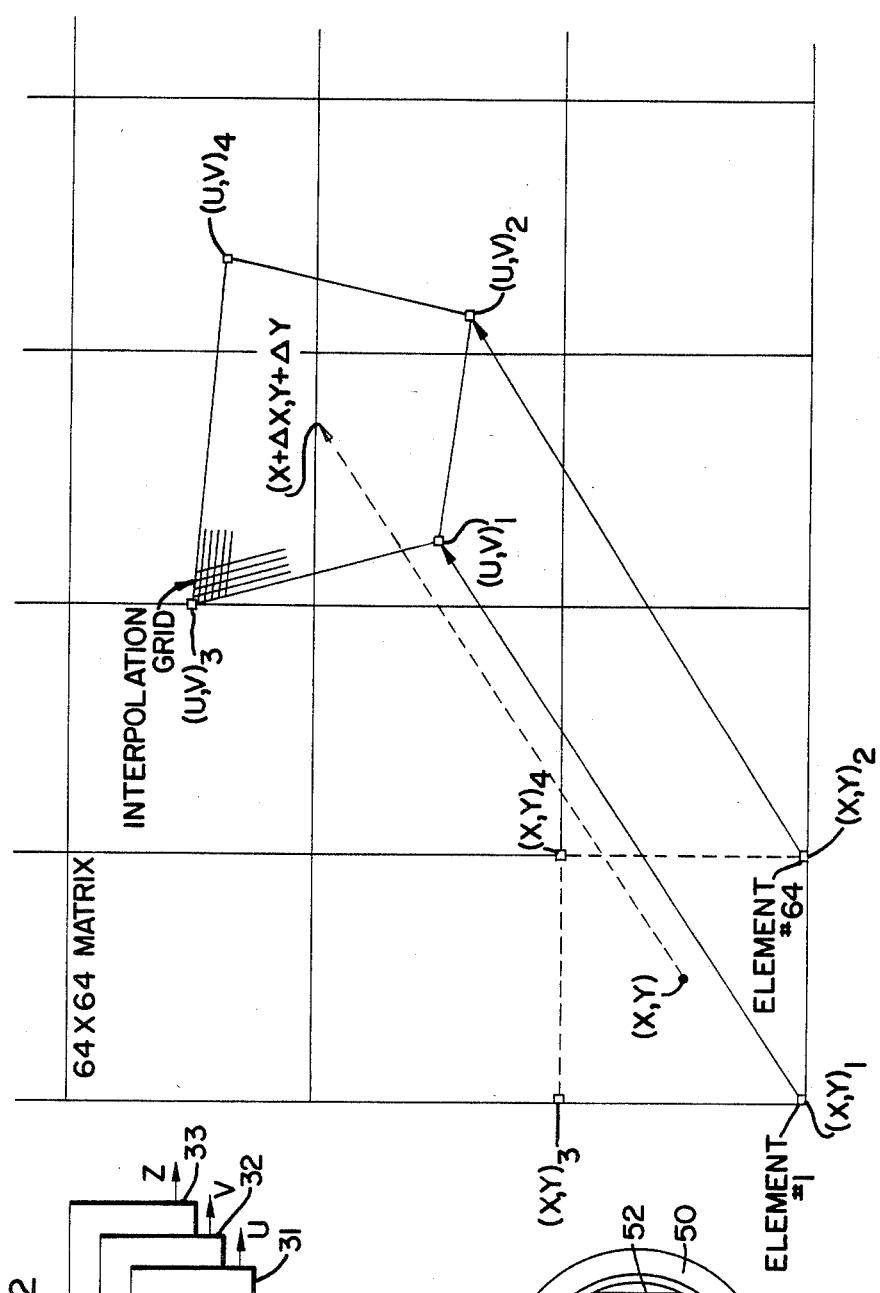
FIG. 3 is a diagramatic representation of an idealized spatial correction of the present invention.
Figure 2:
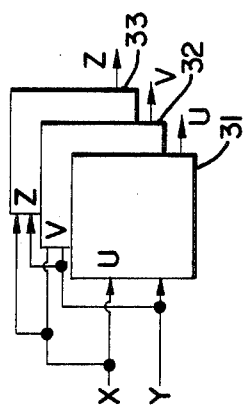
FIG. 2 is a schematic representation of three matrix arrays for the X,Y and Z correction values.

FIG. 2 is a graphical representation of the translation tables. Digitized apparent space coordinates X and Y are input to translation tables 31, 32 producing true spatial coordinates (U, V). With reference to FIG. 3, the 6 MSBs of the digitized X and Y analog coordinates are used to access translation tables 31, 32 obtaining the corresponding true (U, V) coordinates (6 MSB precision) for such position and for each next higher coordinate $(X, Y)_{2-4}$ position in the 64×64 matrices. The translation of these coordinates from an uncorrected (X, Y) mapping to true coordinates (U, V) mapping is shown in solid outline. If succeeding translated corrected elements of the image events were shown they would form a contiguous mosaic without overlapping or voids.

Upon determination of the 6 MSB precision (U, V) corner coordinates of the translated (X, Y) element and assuming a linear relationship in the intervals, a linear proportional interpolation is performed using the 6 LSBs of each X and Y coordinate to find "precise" corrected spatial (U, V) coordinates corresponding to the (X, Y) apparent spatial coordinates of the detected events occurring intermediate or within the translated element area. The procedure involves assuming a linear relationship in both dimensions of the precise location of the detected (X, Y) event within the corrected area defined by $(U, V)_{1-4}$. Given this assumption, $\Delta X$ (delta x) and $\Delta Y$ (delta y) increments are determined and used to precisely locate the apparent event in true space. In this manner there is effectively achieved the precision of correction associated with a 4096×4096 translation table with the economy and ease of calibration associated with a 64×64 matrix.

Figure 4:
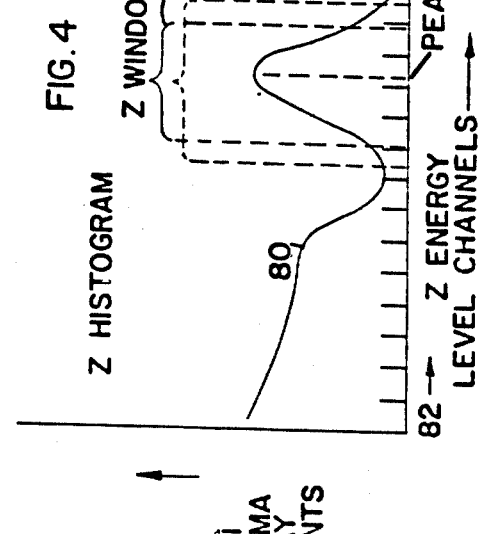
FIG. 4 is a typical energy histogram for an radiation transducer.

As pointed out above, camera Z signal response variation is important from a number of aspects. If a fixed acceptance window is used to select only radiation events of interest, nonuniformity of the image will result from this variation. The prior system corrects most nonuniformity due to Z signal variations by independently presetting the $Z_t$ energy thresholds or "window" for each camera face element of the 64×64 matrix. A typical energy histogram 80 for a gamma camera is shown in FIG. 4. Under normal circumstances, only the peak energy content of the incident radiation is of interest. Therefore, the energy window 81 is selected so that only peak events are recorded. This is accomplished by rejecting all events not displaying a Z level between the upper and lower threshold values of the Z window.

The prior system began normalization of Z camera response by flooding the camera face with a stationary calibration point source so that all areas received energetic events of known intensity. A separate energy histogram or spectra 80, was acquired for each unique 6 MSB (X, Y) apparent space element of the 64×64 matrix array translation table 33 of FIG. 2. In essence, camera responses were sorted by spatial (X, Y) coordinates and by Z signal energy level 82 (the analog energy level is digitized and sorted according to its magnitude in 32 levels, which are also referred to as channels), each level having a event count $N_i$ associated therewith. Using standard peak search and fitting routines on the data accumulated in the histogram a 16 bit word was developed for each element, 8 bits setting the lower $Z_t$ value and the remaining 8 bits setting the higher $Z_t$ value. Once set these values were placed in the Z translation table and accessed by the MSBs of each event. Thereafter, during the camera imaging process (X,Y) events were accepted or rejected according to the predetermined energy window of the matrix element in which they originate.

Thus, the prior system normalized Z signal response by varying the profile of acceptable Z signal energy levels with respect to the apparent space elements defined by the (X,Y) spatial coordinates. The result was a more uniform image response to a flood signal than possible using only spatial corrections.

Although the Z signal normalization procedure of the prior system provides means for the correction of most of the nonuniformity of response due to spatial dependency of Z signal response, it has been observed that there are still some errors in imaging the crystal that are not accounted for. It has been determined that some of these errors are attributable to imperfections in the definition of the acceptable Z window for each element. That determination begins with the following observation of the operation of the prior system: if the camera scintillation crystal is divided into e.g. 64×64 equal elements and a uniform gamma source is applied to the crystal, then when each of the equal areas in apparent space (X, Y) is mapped to an area in corrected or true space (U, V), then each of the areas in (U, V) space should receive an equal number of counts if the correction to (U, V) space was perfect. On the contrary, in practice it is found that the number of counts in each equal section of (U, V) space are not the same. It has been determined that this nonuniformity is due in part to imperfections in the translation table introduced by spatial distortion not completely eliminated during calibration, in part to intrinsic nonuniformity of the camera response, in part to imperfections in the calibration grid, and in part to the limited precision of the mathematical computations.

Figure 5:
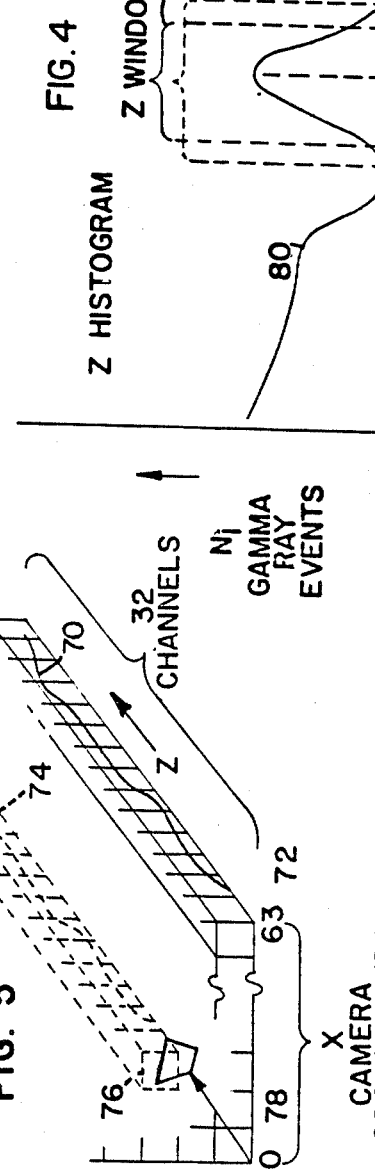
FIG. 5 is a diagramatic representation of a energy histogram flooded in true space compared to prior art correction technique in apparent space.

With these observations in mind, the present invention begins the energy calibration procedure by sorting the multi-channel energy spectra into uniform elements in true (U, V) space. This is in contrast to the prior system in which the energy spectra were sorted into elements in apparent (X, Y) space. Referring to FIG. 5 this difference is graphically illustrated. Energy spectra 70 corresponds to element 72 (X=63, Y=0) of apparent (X, Y) space. In the prior system similar spectra were acquired for all 64×64 matrix elements. The present invention acquires similar spectra but, each of the spectra correspond to corrected (U, V) elements. For example, a portion of the energy events forming spectra 74, which corresponds to true element 76, are derived from energy events detected within element 78 (X=0, Y=0) of apparent space, with the balance of the translated events forming spectrum 74 derived from other elements in apparent space. The same fitting procedures of the prior system are applied to find the centroid $X_c$ and width of the photopeak, to determine the peak energy content of interest, in each of these corrected space spectra. An initial energy window for each of these (U, V) elements is then specified by the user. The energy window is specified by setting a quantity of standard deviations either side of the centroid $X_c$. It will be understood that while in the present invention it is preferable to find, to the greatest practicable degree, the precise centroid $X_c$ of the photopeak, other schemes finding only an approximate centroid $X_c$ could be utilized.

Because of the sources of imperfections noted above, the number of recorded counts occuring within each window determined for each (U, V) element in the camera field of view still may not be completely uniform i,e, certain elements accept more events than others even though all are exposed to a uniform flood signal. Therefore, the present invention provides an adapting step that changes the energy window for each (U, V) element to achieve a condition in which all will incorporate nearly the same number of recorded counts.

The adapting step first determines a target sum to which the counts within each window will be adapted. This target sum (typically an average) is established by inspecting the counts accepted in each true (U, V) element over a selected region of the camera field of view (typically the center portion). Once this target sum has been determined, the window edges or thresholds 81 for each individual (U,V) element are progressively adapted (either shifted, widened or narrowed) until the counts contained within that element are as close as possible to the target sum. These adapted window edges 83 are then incorporated into a Z signal energy translation table by mapping the true (U, V) elements and their corresponding $Z_t$ values back into apparent (X, Y) space using the spatial translation table. The newly defined $Z_t$ values may then be accessed directly by the camera's digitized (X, Y) coordinates without resort to the spatial translation table, thus simplifying the hardware structure and improving the signal processing speed.

To summarize one embodiment the new method of the present invention for determining the Z translation table:
1. Events are detected by the camera, digitized, and translated from apparent (X,Y) to true or corrected (U,V) space.
2. Each event is sorted according to energy level and (U, V) element location.
3. Photopeaks are determined using a standard mathematical fitting routine.
4. Initial Z signal window thresholds $Z_t$ are selected.
5. A target sum is determined by inspecting counts in a specified region of the camera field of view, usually the center of the image.
6. Z window thresholds $Z_t$ for all 64×64 (U, V) matrix elements are progressively adapted until counts are nearly equal to the target sum in all elements.
7. The Z signal window threshold pairs for each (U,V) space element are incorporated into the Z signal table by mapping backwards to apparent (X, Y) space.

It will be seen from the foregoing that the present invention achieves more uniform flood images from radioisotope cameras, allows removal of artifacts in the image created by high-frequency spatial distortion that may not have been completely removed by the prior system, and that the present invention will allow design of gamma cameras to optimize other parameters, such as spatial resolution, at the expense of spatial linearity to an extent not now permitted. In addition, it shall be understood that the present invention may be practiced in other ways than set forth in the preferred embodiment. For example, the adapting step may be utilized whether or not the histograms are compiled with respect to true or apparent spatial elements, and the translating step providing histograms corresponding to true spatial elements may be utilized without the adapting step.

What is claimed is:
1. A signal processing system for radiation imaging apparatus comprising:
   (a) detector means capable of producing an output signal representing apparent orthogonal spatial coordinates and the associated energy level of a radiation event;
   (b) means for determining the energy level distribution of radiation events occurring within predetermined elements in response to an image of known energy level, each of said elements defining a predetermined portion of the apparent image field; and
   (c) means for causing each element to accept substantially the same number of events in response to said image.
2. A signal processing system for use with a radiation imaging apparatus having detector means for producing an output signal representing apparent orthogonal spatial coordinates and the associated energy level of a radiation event, comprising:
   means for determining the energy level distribution and peak energy content of radiation events occurring within predetermined elements in response to an image of known energy level, each of said elements being defined as a predetermined portion of the apparent image field; and
   means for determining an energy window to be accepted for each element in response to a flood image such that every element accepts substantially the same number of events in response to a flood image.
3. A method for calibrating a scintillation radiation camera to provide uniform energy level response at various elements comprising the steps of:
   (a) flooding the camera with a known radiation energy;
   (b) counting the radiation events detected at each energy level within the elements to produce a representation of energy level distribution.
   (c) determining the point about which the photopeak is generally centered for the histogram for each element;
   (d) defining an energy window about said point for one or more elements to set a standard count of acceptable radiation events for all elements; and
   (e) adapting the energy window of each of the elements to cause each to accept a count of radiation events substantially equal to the standard.
4. A method according to claim 3 wherein step (e) includes determining for each element whether the window must be widened or narrowed and then incrementally adjusting the window in the appropriate direction.
5. A signal processing system for radiation imaging apparatus comprising:
   (a) detector means capable of producing an output signal representing the corrected orthogonal spatial coordinates and energy level of a radiation event;
   (b) means for determining the energy level distribution of corrected radiation events within each of a plurality of corrected spatial elements; and
   (c) means for determining for each of said elements the energy window to be accepted in response to a flood image such that every element accepts substantially the same number of events.
6. A method for calibrating a scintillation radiation camera to provide uniform energy level response to detected radiation events comprising the steps of:
   (a) flooding the camera with a known uniform radiation energy;
   (b) accumulating the histograms of the detected radiation events as a function of predetermined corrected spatial coordinate position and magnitude;
   (c) inspecting at least one histogram to set a standard number of acceptable energy events as a function of the histogram or histograms; and
   (d) determining an energy window for each histogram to cause each energy window to include a count of radiation events substantially equal to the standard.

7. In a signal processing system for radiation imaging apparatus having radiation event detector means capable of producing an output signal representing apparent orthogonal spatial element coordinates and their associated energy level for each detected radiation event and means for translating detected events from their apparent spatial element to a corrected spatial element the improved calibration apparatus comprising:
   means for obtaining a histogram of detected radiation events for each corrected spatial element in response to a flood image of known energy level;
   means for determining the point about which the photopeak is generally centered for a histogram;
   means for defining an energy window about said point for at least one element to set a standard number of acceptable radiation events for the elements; and
   means for adapting the energy windows of the elements to cause each element to accept a count of radiation events substantially equal to the standard.

8. An improved signal processing system including improved calibration apparatus for use with a radiation imaging apparatus, comprising:
   (a) a radiation transducer for producing signals proportional to the apparent orthogonal spatial coordinates and proportional to the energy level of detected radiation events;
   (b) means operative in a spatial calibration mode for storing corrected spatial coordinates corresponding to a plurality of predetermined apparent spatial coordinates relative to selected detected radiation events;
   (c) means for translating apparent spatial coordinates to corrected spatial coordinates, said translating means communicating with said means for storing;
   (d) means for interpolating the corrected spatial coordinates of the detected radiation events occurring within the space bounded by said stored corrected spatial coordinates to produce precise corrected spatial coordinates;
   (e) means operative in an energy level calibration mode using coordinates derived from said translating means for obtaining a histogram for each corrected spatial element;
   (f) means operative in said energy level calibration mode for setting a window of acceptable energy levels;
   (g) means operative in said energy level calibration mode for determining the number of counts in response to a flood image occurring within said window for each corrected spatial element;
   (h) means operative in said energy level calibration mode for progressively adapting the window for each element until all of said elements accept substantially the same number of counts in response to the flood image;
   (i) means operative in said energy level calibration mode for storing one or more of said windows as a function of apparent spatial coordinates;
   (j) means for comparing the energy level of the transducer signals of the detected radiation events to the windows corresponding to the apparent spatial coordinates of the events; and
   (k) output means for producing an output signal, said output means being responsive to said transducer signals and to said comparing means so that only those transducer signals occurring within the windows contribute to form said output signal.

9. A signal processing system for radiation imaging apparatus having;
   (a) detector means for producing an output signal representing corrected orthogonal spatial coordinates and the associated energy level of a radiation event;
   (b) means for obtaining an energy level histogram of radiation events occurring within predetermined elements in response to a flood image of know energy level, each of said elements being defined as a predetermined portion of the corrected image field;
   (c) means for determining a center of the peak for each of said histograms; and
   (d) means for presetting an energy window to be accepted in response to a flood image, the center of said window being substantially coincidental with the determined center of the peak of each element.

10. A method for calibrating a scintillation radiation camera to provide uniform energy level response to detected radiation events comprising the steps of:
   (a) flooding the camera with a known uniform radiation energy;
   (b) translating detected events from their apparent spatial element to corrected spatial elements;
   (c) counting the radiation events at each of a plurality of discrete energy levels within each of said corrected spatial elements to produce an energy histogram for each corrected spatial element;
   (d) determining a peak centroid of each histogram;
   (e) defining an energy window to be centered about said peak centroid of all elements.

11. A signal processing system for radiation imaging apparatus comprising:
   (a) detector means capable of producing an output signal representing the corrected orthogonal spatial coordinates and energy level of a radiation event;
   (b) means for determining the energy level distribution of corrected radiation events within each of a plurality of uniform corrected spatial elements; and
   (c) means for determining for each of said elements the energy window to be accepted in response to a flood image such that every element accepts substantially the same number of events.

12. A signal processing system for radiation imaging apparatus comprising:
   (a) detector means capable of producing an output signal representing the corrected orthogonal spatial coordinates and energy level of a radiation event;
   (b) means for determining the energy level distribution of corrected radiation events within each of a plurality of equal sections of a corrected image; and
   (c) means for determining for each of said equal sections the energy window to be accepted in response to a flood image such that every equal section accepts substantially the same number of events.

13. A method for calibrating a scintillation radiation camera to provide uniform energy level response to detected radiation events comprising the steps of:
   (a) flooding the camera with a known uniform radiation energy;

(b) accumulating the histograms of the detected radiation events as a function of predetermined corrected spatial coordinate position and magnitude, said function producing histograms each corresponding to one of a plurality of uniform areas of the corrected spatial image;

(c) inspecting at least one histogram to set a standard number of acceptable energy events as a function of the histogram or histograms; and (d) determining an energy window for each histogram to cause each energy window to include a count of radiation events substantially equal to the standard.

14. In a signal processing system for radiation imaging apparatus having radiation event detector means capable of producing an output signal representing apparent orthogonal spatial event coordinates and their associated energy level for each detected radiation event and means for translating detected events from their apparent spatial position to a corrected spatial position the improved calibration apparatus comprising:

(a) means for obtaining a histogram of detected radiation events for each of a plurality of uniform corrected spatial elements in response to a flood image of known energy level;

(b) means for determining the point about which the photopeak is generally centered for a histogram;

(c) means for defining an energy window about said point for at least one element to set a standard number of acceptable radiation events for the elements; and (d) means for adapting the energy windows of the elements to cause each element to accept a count of radiation events substantially equal to the standard.

15. An improved signal processing system including improved calibration apparatus for use with a radiation imaging apparatus, comprising:

(a) a radiation transducer for producing signals proportional to the apparent orthogonal spatial coordinates and proportional to the energy level of detected radiation events;

(b) means operative in a spatial calibration mode for storing corrected spatial coordinates corresponding to a plurality of predetermined apparent spatial coordinates relative to selected detected radiation events;

(c) means for translating apparent spatial coordinates to corrected spatial coordinates, said translating means communicating with said means for storing;

(d) means for interpolating the corrected spatial coordinates of the detected radiation events occurring within the space bounded by said stored corrected spatial coordinates to produce precise corrected spatial coordinates;

(e) means operative in an energy level calibration mode using coordinates derived from said translating means for defining a plurality of uniform corrected spatial elements and obtaining a histogram for each corrected spatial element;

(f) means operative in said energy level calibration mode for setting a window of acceptable energy levels;

(g) means operative in said energy level calibration mode for determining the number of counts in response to a flood image occurring within said window for each corrected spatial element;

(h) means operative in said energy level calibration mode for progressively adapting the window for each element until all of said elements accept substantially the same number of counts in response to a flood image;

(i) means operative in said energy level calibration mode for storing one or more of said windows as a function of apparent spatial coordinates;

(j) means for comparing the energy level of the transducer signals of the detected radiation events to the windows corresponding to the apparent spatial coordinates of the events; and (k) output means for producing an output signal, said output means being responsive to said transducer signals and to said comparing means so that only those transducer signals occurring within the windows contribute to form said output signal.

16. A signal processing system for radiation imaging apparatus having;

(a) detector means for producing an output signal representing corrected orthogonal spatial coordinates and the associated energy level of a radiation event;

(b) means for obtaining an energy level histogram of radiation events occurring within predetermined elements of equal area in response to a flood image of know energy level, each of said elements being defined as a predetermined portion of the corrected image field;

(c) means for determining a center of the peak for each of said histograms; and (d) means for presetting an energy window to be accepted in response to a flood image, the center of said window being substantially coincidental with the determined center of the peak of each element.

17. A method for calibrating a scintillation radiation camera to provide uniform energy level response to detected radiation events comprising the steps of:

(a) flooding the camera with a known uniform radiation energy;

(b) translating detected events from their apparent spatial element to corrected spatial elements of uniform area;

(c) counting the radiation events at each of a plurality of discrete energy levels within each of said corrected spatial elements to produce an energy histogram for each corrected spatial element;

(d) determining a peak centroid of each histogram;

(e) defining an energy window to be centered about said peak centroid of all elements.

* * * * *

UNITED STATES PATENT AND TRADEMARK OFFICE
CERTIFICATE OF CORRECTION

PATENT NO. : 4,546,255

DATED : October 8, 1985

INVENTOR(S) : Knoll et al.

It is certified that error appears in the above-identified patent and that said Letters Patent is hereby corrected as shown below:

Column 1, line 64, "non-linearities" should be --nonlinearities--;

Column 2, line 51, "an" should be --a--;

Column 3, line 2, "a" should be --an--;

Column 3, line 41, "an should be --a--;

Column 3, line 43, "a" should be --an--;

Column 3, line 63, delete "an";

Column 10, line 12, "know" should be "known";

Column 12 line 36, "know" should be --known--;

Signed and Sealed this

Twenty-fourth Day of June 1986

[SEAL]

Attest:

DONALD J. QUIGG

Attesting Officer

Commissioner of Patents and Trademarks